US008658684B2

(12) United States Patent     (10) Patent No.: US 8,658,684 B2
Yin et al.     (45) Date of Patent: Feb. 25, 2014

(54) PHARMACEUTICAL COMPOSITION AND ITS USE IN THE PREPARATION OF A MEDICAMENT FOR THE TREATMENT OF CEREBROVASCULAR DISEASES

(75) Inventors: Xiaojin Yin, Nanjing (CN); Shibao Yang, Nanjing (CN); Xiaoqiang Li, Nanjing (CN); Zheng Jiang, Nanjing (CN); Jian He, Nanjing (CN); Anyuan Zhang, Nanjing (CN); Xin Huang, Nanjing (CN)

(73) Assignee: Jiangsu Simcere Pharmaceutical R & D Co., Ltd., Nanjing (CH)

( * ) Notice: Subject to any disclaimer, the term of this patent is extended or adjusted under 35 U.S.C. 154(b) by 401 days.

(21) Appl. No.: 12/920,579

(22) PCT Filed: Mar. 3, 2009

(86) PCT No.: PCT/CN2009/070612
§ 371 (c)(1),
(2), (4) Date: Sep. 1, 2010

(87) PCT Pub. No.: WO2009/109132
PCT Pub. Date: Sep. 11, 2009

(65) Prior Publication Data
US 2011/0003873 A1   Jan. 6, 2011

(30) Foreign Application Priority Data
Mar. 4, 2008 (CN) .......................... 2008 1 0020387

(51) Int. Cl.
*A61K 31/415* (2006.01)
(52) U.S. Cl.
USPC .......................................................... 514/404
(58) Field of Classification Search
USPC .......................................................... 514/404
See application file for complete search history.

(56) References Cited

U.S. PATENT DOCUMENTS

| | | | | |
|---|---|---|---|---|
| 4,857,542 | A | 8/1989 | Nishi et al. | 514/404 |
| 5,837,723 | A | 11/1998 | Watanabe | 514/404 |
| 6,933,310 | B1 | 8/2005 | Ikeda | 514/403 |
| 7,211,596 | B2 | 5/2007 | Yoshida et al. | 514/404 |
| 2005/0009896 | A1 | 1/2005 | Yamada et al. | 514/404 |
| 2007/0021448 | A1 | 1/2007 | Han et al. | 514/267 |
| 2007/0148217 | A1 | 6/2007 | Mori et al. | 424/449 |
| 2007/0249700 | A1 | 10/2007 | Yuki et al. | 514/407 |
| 2008/0161378 | A1 | 7/2008 | Yoshino et al. | 514/404 |
| 2010/0221245 | A1 | 9/2010 | Kunin | 424/133.1 |

FOREIGN PATENT DOCUMENTS

| | | |
|---|---|---|
| CN | 1525856 | 9/2004 |
| CN | 1823922 | 8/2006 |
| CN | 1846740 | 10/2006 |
| CN | 101239053 A | 8/2008 |
| EP | 0 208 874 A1 | 1/1987 |
| EP | 0 208 874 B1 | 1/1987 |
| EP | 1 386 606 | 2/2004 |
| EP | 1 437 137 | 7/2004 |
| JP | 2003/081830 | 3/2003 |
| JP | 2004/123716 | 4/2004 |
| JP | 2005/029573 | 2/2005 |
| JP | 2006/052172 | 2/2006 |
| JP | 2007-505936 A | 3/2007 |
| JP | 2007-529431 A | 10/2007 |
| JP | 2008/001605 | 1/2008 |
| JP | 2008/001606 | 1/2008 |
| JP | 2008/001607 | 1/2008 |
| JP | 2009/143902 | 7/2009 |
| WO | 02/092082 A1 | 11/2002 |
| WO | 2006/016707 | 2/2006 |

OTHER PUBLICATIONS

Liang et al., "The Effect of Borneol on Evan's Blue Staining of Rabbit and Rat Brain Tissue," *Journal of Guangzhou University of Traditional Chinese Medicine (Chinese)*, vol. 10 (No. 4): pp. 211-213, 1993.
He et al., "The protective effect of Borneol on experimental cerebral ischemia," *Journal of Guangdong College of Pharmacy*, 22 (2): 171-173, 2006.
Li et al., "The antithrombotic effect of borneol related to it anticoagulant property," *Am. J. Chin. Med.* 36(4):719-727, 2008 (abstract only).
Liu et al., "The Influence of Borneol on the Passing of Gentamycin Through Blood-Brain Barrier," *Journal of Guangzhou Chinese Medicine University* 11(1):37-40, 1994 (w/ English abstract).
Mayhan et al., "Nitric oxide accounts for histamine-induced increases in macromolecular extravasation," *Am. J. Physiol.* 266(Heart Circ. Physiol. 35):H2369-H2373, 1994.
Mayhan et al., "Role of nitric oxide in histamine-induced increases in permeability of the blood-brain barrier," *Brain Research* 743:70-76, 1996.
Sanovich et al., "Pathway across blood-brain barrier opened by the bradykinin agonist, RMP-7," *Brain Research* 705:125-135, 1995.
Xu et al., "Effect of menthol and borneol on the distribution of sulfadiazine sodium and Evan's blue in the rat and mouse brain," *Chinese Medicine Pharmacology and Clinical Study* 6:31-33, 1995 (w/ English abstract).
Zhao et al., "Comparison Between Borneol-Induced Opening of Blood-Brain Barrier and its Pathological Opening," *New Chinese Medicine and Clinical Pharmacology* 13(5):287-288, 2002 (w/ English abstract, key words and introduction).
Zhao et al., "The relationship between eNOS and the function of borneol in stimutating the BBB's opening," *Journal of Brain and Neurological Diseases* 9(4):207-209, 2001 (w/ English abstract).
"Clinical observation of Butylphthalide in treatment of acute ischemic stroke," *Chinese Remedies & Clinics* 10(1):89-90, 2010 (w/English translation of relevant portion).
"Clinical observation of intravenous thrombolysis with urokinase in treatment of acute ischemic stroke," *China Foreign Medical Treatment* 9:110-112, 2010 (w/English translation of relevant portion).

(Continued)

*Primary Examiner* — San-Ming Hui
(74) *Attorney, Agent, or Firm* — Seed IP Law Group PLLC

(57) ABSTRACT

A pharmaceutical composition comprises 3-methyl-1-phenyl-2-pyrazolin-5-one and borneol, and can be used to prepare the medicine for treating cerebrovascular diseases.

14 Claims, No Drawings

(56) References Cited

OTHER PUBLICATIONS

"Clinical observation of urinary kallidinogenase injection in treatment of ischemic stroke," *China Practical Medicine* 5(13):140-141, 2010 (w/English translation of relevant portion).

"Quantitative analysis of combined drug," *Chinese Pharmacological Bulletin* 14(5):479-480, 1998 (w/English translation of relevant portion).

English translation of Japanese Office Action, mailed Oct. 30, 2012, for Japanese Application No. 2010-547939, 5 pages.

PHARMACEUTICAL COMPOSITION AND ITS USE IN THE PREPARATION OF A MEDICAMENT FOR THE TREATMENT OF CEREBROVASCULAR DISEASES

The present application claims the priority of Chinese Patent Application No. 200810020387.1 filed on Mar. 4, 2008 and entitled "A Composition Comprising 3-methyl-1-phenyl-2-pyrazolin-5-one", which is incorporated into herein by reference in its entirety.

FIELD OF THE INVENTION

The present invention relates to a pharmaceutical composition and the use thereof in the preparation of a medicament for the treatment of cerebrovascular diseases.

BACKGROUND OF THE INVENTION

Cerebrovascular diseases (CVD) are a group of diseases which are severely harmful to human health and have currently become one of important factors for human disability and mortality.

Cerebrovascular disease refers to a brain disorder due to cerebrovascular abnormality. Stroke generally refers to acute cerebrovascular disease.

Cerebrovascular diseases can be simply divided into two classes: (1) ischemic cerebrovascular disease caused by reduced or blocked blood flow, and (2) hemorrhagic cerebrovascular disease caused by broken blood vessel. Ischemic cerebrovascular diseases are mainly manifested as cerebral infarctions (including cerebral thrombosis and cerebral embolism). Additionally, another manifestation of ischemic cerebrovascular disease is called transient ischemic attack (TIA, usually abbreviated by doctors), which can be completely recovered within 24 hours without any sequela. Hemorrhagic cerebrovascular diseases can be further divided into two classes: (1) cerebral hemorrhage, in which blood vessel is broken and the blood flows into cerebral parenchyma; and (2) subarachnoid hemorrhage (SAH, abbreviated by doctors), in which blood vessel is broken and the blood flows into subarachnoid space surrounding the brain.

3-methyl-1-phenyl-2-pyrazolin-5-one, also called Edaravone, has a structural formula of

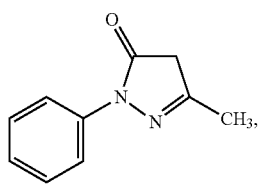 [SMILES: CC1=NN(c2ccccc2)C(=O)C1]

a molecular formula of $C_{10}H_{10}N_2O$ and a molecular weight of 174.19.

3-methyl-1-phenyl-2-pyrazolin-5-one is a brain protective agent, which scavenges free radicals, inhibits lipid peroxidation, and thereby inhibits oxidative damages of brain cells, vascular endothelial cells and nerve cells. Intravenous administration of Edaravone into rats after ischemia/reperfusion suppresses the development of cerebral edema and cerebral infarction, relieves accompanying neurological symptoms and inhibits delayed neuronal death. It has been found that 3-methyl-1-phenyl-2-pyrazolin-5-one, with clinical dosage of 60 mg/day for an adult, has some side and adverse effects such as acute renal failure to uncertain extent, liver dysfunction, thrombocytopenia, diffuse intravascular thrombosis.

Borneol, commonly used in Chinese traditional medicine, is known as a resuscitation-inducing aromatic herbal agent and primes other drugs to the upper. Borneol is generally used as a priming agent to promote the efficacies of other drugs. It is indicated in *Augmented Materia Medica* (Bencao Yanyi) that borneol is poor when used alone and instead significant when used as an adjuvant.

SUMMARY OF THE INVENTION

An objective of the present invention is to provide a pharmaceutical composition comprising 3-methyl-1-phenyl-2-pyrazolin-5-one and borneol. The pharmaceutical composition in combination has synergistic effect and improved efficacies for the treatment of cerebrovascular diseases.

Preferably, the weight ratio of 3-methyl-1-phenyl-2-pyrazolin-5-one to borneol is from 4:1 to 1:4, and more preferably from 2:1 to 1:2.

Said borneol includes natural borneol and synthetic borneol, and natural borneol is preferably used. The natural borneol recited in *Pharmacopoeia of People's Republic of China*, 2005 Ed, that is dextro-camphol (LongNao), may be used.

The above pharmaceutical compositions may further comprise a solvent, which can facilitate the mixing of 3-methyl-1-phenyl-2-pyrazolin-5-one and borneol. The solvent may be selected from a group consisting of water-soluble organic solvent or a mixture of water-soluble organic solvent and water. Commonly used water-soluble organic solvents include but not limited to alcohol solvents, ether solvents and ketone solvents. Commonly used alcohol solvents include but not limited to ethanol, isopropanol, ethylene glycol and propylene glycol. Commonly used ether solvents include but not limited to ethylene glycol monoethyl ether and ethylene glycol monobutyl ether. Commonly used ketone solvents include but not limited to acetone and N-methyl-2-pyrrolidone. Preferably, the water-soluble organic solvent is propylene glycol.

Another objective of the present invention is to provide use of the above pharmaceutical composition in the preparation of a medicament for the treatment of cerebrovascular diseases.

Preferably, the above pharmaceutical composition is used in the preparation of a medicament for the treatment of ischemic cerebrovascular disease or cerebral infarction.

The pharmaceutical composition provided herein comprises 3-methyl-1-phenyl-2-pyrazolin-5-one and borneol, has synergistic effect in the treatment of cerebrovascular diseases and thereby has significantly improved efficacies. Accordingly, the pharmaceutical composition may have a reduced dosage 3-methyl-1-phenyl-2-pyrazolin-5-one and is still effective, and thereby has a reduced toxicity.

DETAILED DESCRIPTION OF THE INVENTION

The present invention is further described with reference to the following examples. Edaravone recited in the examples is 3-methyl-1-phenyl-2-pyrazolin-5-one. Natural borneol recited is that recorded in *Pharmacopoeia of People's Republic of China* (2005 edition), namely dextro-camphol.

Example 1

2 g of Edaravone is added to and completely dissolved by agitation in a solution of 200 g of propylene glycol. Then water for injection is added slowly and dissolves the mixture to a volume of 1000 mL.

Example 2

2 g of synthetic borneol is added to and completely dissolved by agitation in a solution of 200 g of propylene glycol. Then water for injection is added slowly and dissolves the mixture to a volume of 1000 mL.

Example 3

2 g of natural borneol is added to and completely dissolved by agitation in a solution of 200 g of propylene glycol. Then water for injection is added slowly and dissolves the mixture to a volume of 1000 mL.

Example 4

2 g of Edaravone and 1 g of synthetic borneol are added to and completely dissolved by agitation in a solution of 200 g of propylene glycol. Then water for injection is added slowly and dissolves the mixture to a volume of 1000 mL.

Example 5

2 g of Edaravone and 1 g of natural borneol are added to and completely dissolved by agitation in a solution of 200 g of propylene glycol. Then water for injection is added slowly and dissolves the mixture to a volume of 1000 mL.

Example 6

1 g of Edaravone and 2 g of natural borneol are added to and completely dissolved by agitation in a solution of 100 g of propylene glycol. Then water for injection is added slowly and dissolves the mixture to a volume of 1000 mL.

Example 7

4 g of Edaravone and 1 g of natural borneol are added to and completely dissolved by agitation in a solution of 400 g of propylene glycol. Then water for injection is added slowly and dissolves the mixture to a volume of 1000 mL.

Example 8

1 g of Edaravone and 1 g of natural borneol are added to and completely dissolved by agitation in a solution of 200 g of propylene glycol. Then water for injection is added slowly and dissolves the mixture to a volume of 1000 mL.

Example 9

1 g of Edaravone and 2 g of natural borneol are added to and completely dissolved by agitation in a solution of 200 g of propylene glycol. Then water for injection is added slowly and dissolves the mixture to a volume of 1000 mL.

Example 10

2 g of Edaravone and 0.5 g of natural borneol are added to and completely dissolved by agitation in a solution of 200 g of propylene glycol. Then water for injection is added slowly and dissolves the mixture to a volume of 1000 mL.

Example 11

4.5 g of Edaravone and 0.5 g of natural borneol are added to and completely dissolved by agitation in a solution of 400 g of propylene glycol. Then water for injection is added slowly and dissolves the mixture to a volume of 1000 mL.

Example 12

2 g of Edaravone and 1 g of natural borneol are added to and completely dissolved by agitation in a solution of 100 g of propylene glycol. Then water for injection is added slowly and dissolves the mixture to a volume of 1000 mL.

Example 13

8 g of Edaravone and 4 g of natural borneol are added to and completely dissolved by agitation in a solution of 500 g of propylene glycol. Then water for injection is added slowly and dissolves the mixture to a volume of 1000 mL.

Example 14

2 g of Edaravone is added to and completely dissolved by agitation in a solution of 100 g of propylene glycol. Then water for injection is added slowly and dissolves the mixture to a volume of 1000 mL.

Example 15

8 g of Edaravone is added to and completely dissolved by agitation in a solution of 400 g of propylene glycol. Then water for injection is added slowly and dissolves the mixture to a volume of 1000 mL.

Examples 16-19 are examples for comparison of efficacies.

Example 16

1. Materials and Methods 1.1 Animals: healthy male Wistar rats weighing 280-320 g.

1.2 Drugs and Reagents: Edaravone for injection (2 mg/mL) of Example 1, natural borneol injection (2 mg/mL) of Example 3 and Edaravone+natural borneol injection of Example 5.

1.3 Methods 1.3.1 Preparation of Focal Cerebral Ischemia Reperfusion Model

Main steps are described as follows. Rats were anesthetized with 10% chloral hydrate (350 mg/kg, i.p.). Right external carotid was separated, ligated and severed. A nylon thread with rounded tip was inserted slowly for about 18 mm in depth into the residual end of right external carotid and through common carotid and internal carotid to induce ischemia by blocking the origin of middle cerebral artery. After ischemia for 2 h, the nylon thread was removed for reperfusion for 24 h. Animals in the sham group were treated identically to those in the model group, except that a nylon thread was just used to separate the artery. Manifestation of Homer's symptom and opposite lateral body dyskinesia after animal revival means a successful modelling.

1.3.2 Animal Grouping and Administration

Experimental animals were randomly divided into five groups, including sham group, control group and drug groups. Animals in drug groups were intraperitoneally injected twice, 30 min before ischemia and 12 h after reperfusion. Animals in sham group and control group were each injected with equal volume of normal saline instead.

1.3.3 Determination of neurological deficit Scoring, Cerebral Infarction Size and Cerebral Water Content Neurological deficit scoring: Behavioral evaluation was performed 24 h after reperfusion according to Longa 5-point scoring system.

Determination of cerebral infarction size: Animals were decapitated to get the brain after the last neurological deficit scoring. Rhinencephalon, lower brain stem and cerebella were removed, and the remaining brains were immediately weighted to obtain wet weights. The brains were sectioned coronally into five slices with substantially identical thickness on ice, then incubated in 2,3,5-triphenyl tetrazolium chloride for 30 min at 37° C. Normal brain tissues appeared rose, while infarction areas appeared white. Next, brain slices were fixed in 10% formaldehyde, and white tissues were carefully removed and weighed. Infarction size was determined by the percentage of infracted tissue weight in the total cerebral weight.

Determination of cerebral water content: Cerebral water contents were determined by dry and wet method. Animals were sacrificed to get the whole brain. Rhinencephalon, lower brain stem and cerebella were removed and the wet weight of the remaining brains was determined immediately. Dry weight was obtained after baking in a oven for about 18 h at 120° C. Cerebral water content was calculated according to the following equation: Cerebral water content (%)=(cerebral wet weight−cerebral dry weight)/cerebral wetweight×100.

2. Results 2.1 Effects on Cerebral Infarction Size and Neurological Deficit Score after Ischemia/Reperfusion The infarction size after ischemia reperfusion was significantly reduced in rats of all drug groups (P<0.01) compared with those of control group. Neither Edaravone alone nor natural borneol alone had significant effect on symptoms of neurological deficits in rats. However, the combination of Edaravone and natural borneol significantly ameliorated symptoms of neurological deficits, indicating that the two drugs have synergistic effect. Results were shown in table 1.

TABLE 1

Effects on cerebral infarction size and neurological deficit score after ischemia/reperfusion ($\bar{x} \pm S$) (mean ± SD)

| Group | Cerebral infarction size (%) | neurological deficit score (points) |
|---|---|---|
| control | 35.7 ± 7.52 | 3.1 ± 1.05 |
| Edaravone (1.0 mg · kg$^{-1}$) | 18.0 ± 5.29 ** | 2.5 ± 1.02 |
| Natural borneol (0.5 mg · kg$^{-1}$) | 19.8 ± 6.37 ** | 2.0 ± 0.98 |
| Combination (0.5 mg · kg$^{-1}$ Edaravone + 0.25 mg · kg$^{-1}$ Natural borneol) | 18.1 ± 3.61 ** | 1.1 ± 0.69 * |

* P<0.05, ** P<0.01, compared with control group.

2.2 Effects on Cerebral Water Content after Ischemia/Reperfusion

Cerebral edema induced by ischemia/reperfusion was significantly reduced in rats of all drug groups. Both Edaravone alone and natural borneol alone had significant effect on cerebral water content compared with control group (P<0.05). The combination of Edaravone and natural borneol had highly significant effect on cerebral water content compared with control group (P<0.01), indicating that the two drugs have synergistic effect. Results were shown in Table 2.

TABLE 2

Effects on cerebral water content after ischemia/reperfusion ($\bar{x} \pm S$) (mean ± SD)

| Group | Cerebral water content (%) |
|---|---|
| Sham | 78.41 ± 1.15 |
| control | 82.19 ± 1.07 |
| Edaravone (1.0 mg · kg$^{-1}$) | 81.65 ± 1.24 * |
| Natural borneol (0.5 mg · kg$^{-1}$) | 81.25 ± 0.97 * |
| Combination (0.5 mg · kg$^{-1}$ Edaravone + 0.25 mg · kg$^{-1}$ natural borneol) | 80.12 ± 1.43 ** |

* P<0.05, ** P<0.01, compared with control group.

Example 17

1. Materials and Methods 1.1 Animals: Healthy male Wistar rats weighing 280-320 g 1.2 Drugs and Reagents: Edaravone+natural borneol for injection of Examples 5, 8 and 9.

1.3 Methods 1.3.1 Preparation of Focal Cerebral Ischemia/Reperfusion Model

Middle cerebral artery occlusion (MCAO), a cerebral ischemia/reperfusion model, was prepared using the internal carotid thread method. Animals were anesthetized with 10% chloral hydrate (3.5 mL/kg), and then fixed on the operation table in prone position. The skin was disinfected and the neck was incised from the midline. Right common carotid, external carotid and internal carotid were separated, and vagus nerve was separated carefully. The external carotid was ligated and severed. Moved forward along the internal carotid, and then pterygopalatine artery was ligated. The proximal part of common carotid was clamped and a cut was made at the distal end of the external carotid ligature. A nylon thread with the outer diameter of 0.285 mm was inserted into the cut, through the branch of common carotid and then into internal carotid slowly until a slight resistance was met (about 20 mm distance from the divergence point). Blood supply in middle cerebral artery was thereby completely blocked. Cerebral blood flow was monitored by using laser Doppler cerebral flowmetry. After ischemia in the right brain for 2.0 h, the nylon thread was withdrawn slowly and then blood supply was recovered for reperfusion. The scalp was sutured and disinfected. In the sham group, only the blood vessels were separated without the insertion of a nylon thread. During the operation, rat heating plate and desk lamp with 60 W were used to keep the body temperature of rats at 37.0±0.5° C.

1.3.2 Animal Grouping and Administration

Experimental animals were randomly divided into six groups, including sham group, model group, positive control group and drug groups (the total dosage of Edaravone+natural borneol was 0.75 mg/kg). After cerebral ischemia was modeled in experimental animals, all animals were divided into the groups in a single-blind manner with identical probability. Respective drugs were administrated once immediately after cerebral ischemia, and then administrated sequentially after 2, 4 and 24 hours. The four administrations were made totally to each animal. Rats in model group were injected through tail vein with equal volume of normal saline. Rats in sham group were injected through tail vein with equal volume of normal saline. Rats in positive control group were administrated with Nimodipine injection. The dosage in positive control group was 1.2 mg/kg per animal for three dosages and a single dosage was 0.4 mg/kg each animal.

1.3.3 Neurological Deficit Scoring and Cerebral Infarction Size Determination

Neurological deficit scoring: neurological deficit symptoms were evaluated according to modified Bederson scoring system of 5-point. Neurological deficit symptoms after cerebral trauma in rats were evaluated by using single-blinded method. That is, the experiment designer labeled the animals in groups, while the experiment performer who scored neurological deficit symptoms were blinded for animals grouping. After the evaluation was finished, the scorer presented the scoring result of the labeled animals to the designer. The designer unblinded the experiment and obtained the score of each animal in respective groups.

Neurological Deficit Scoring: the detail criterion of Bederson 5-point scoring system is:

0: Both forelimbs of the animal extend toward the floor when the animal keeps suspended by holding the animal's tail, and no other behavioral defect is observed.

1: The animal on its (left) forelimb opposite to the injured side shows wrist and elbow flexion, shoulder adduction, elbow abduction and close attachment to the chest wall.

2: When placing the animal on a smooth plate and pushing the shoulder on the injured side toward the opposite side, a reduced resistance is met.

3: When walks freely, the animal makes circular movement opposite to the injured side.

4: The animal shows flaccid and paralyzed limbs and has no active limb movement.

Determination of cerebral infarction area and brain lesion: The animal was anesthetized with 10% chloral hydrate and decapitated to get the brain. After Rhinencephalon, cerebella and lower brain stem were removed, blood on the brain surface was washed with normal saline and residual water on the surface were blotted up. After being placed at −80° C. for 7 min, the brain was taken out and immediately coronal section was vertically and downward made from the optic chiasma, and thereby the brain was cut into slices backwards every 2 mm. Brain slices were immersed in 20 g/L TTC staining solution (37° C., 90 min) formulated freshly in 0.2 mol/L PBS pH 7.4-7.8. Normal brain tissues were stained crimson, while ischemic brain tissues appeared white. After rinsed with normal saline, brain slices were arranged in a row sequentially and rapidly. Residual water on the surface were blotted up and the slices were photographed. The left and right brain tissues were separated and weighed respectively as $W_{left}$ (weight of left brain) and $W_{right}$ (weight of right brain). 15 mL freshly formulated exaction solution (DMSO (dimethyl sulfoxide): ethanol=1:1) was added to left and right brain tissues respectively. The tissues were extracted at 25° C. for 24 hours in dark. The generated red substance, formazan, was extracted sufficiently until the brain slices turned white.

(1) analysis of the photos were made by using image analysis software. Right ischemia area (white) and right total area were marked and the percentage of infarction area was calculated by the following formula:

$$\text{Cerebral infarction area } \% = 100 \times \frac{\text{Total ischemia area}}{\text{Right total area}}$$

(2) The absorbance of the respective exacts (extract 100 μL+extract solution 1900 μL) was determined at 485 nm and was averaged from four independent determinations to produce $A_{left}$ and $A_{right}$. The percentage of brain lesion was calculated by the following formula:

$$\text{brain lesion } \% = 100 \times \left(1 - \frac{A_{right} \times W_{left}}{A_{left} \times W_{right}}\right)$$

1.3.4 Statistical analysis Quantitative data were expressed in mean±SD. Cerebral infarction area and neurological deficit score were evaluated by one-way ANOVA. The significance of difference between two groups was determined by Scheffe's test. Animal mortality was compared between groups by $X^2$ test. $P<0.05$ was defined as significant difference.

2. Results 2.1 Effects on Neurological Deficit Symptoms

The score of neurological deficit symptoms were shown in Table 3. Compared with model group, formulations of Edaravone and natural borneol in various ratios and Nimodipine significantly ameliorated neurological deficit symptoms ($F_{4,35}=14.59$, $P=0.000$). It was shown that Edaravone and natural borneol in combination can ameliorate neurological deficit symptoms significantly.

TABLE 3

Effects of Edaravone (A) and natural borneol (B) in combination on neurological deficit symptoms

| Group | Model | Nimodipine | A:B = 2:1 | A:B = 1:1 | A:B = 1:2 |
|---|---|---|---|---|---|
| mean ± SD | 2.6 ± 0.52 | 1.1 ± 0.58 * | 0.81 ± 0.26 * | 1.1 ± 0.35 * | 1.5 ± 0.76 * |

X ± SD, n = 8;
* P < 0.05, compared with model group.

2.2 Effects on Cerebral Infarction Area

Cerebral infarction areas in various groups were shown in Table 4. Compared with model group, treatment by Edaravone and natural borneol in ratios of 2:1 and 1:1, and by Nimodipine significantly reduced cerebral infarction area ($F_{4,35}=5.38$, $P=0.002$). Compared with model group, treatment by Edaravone and natural borneol in a ratio of 1:2 has the tendency to reduce cerebral infarction area ($F_{4,35}=5.38$, $P=0.358$).

TABLE 4

Effects of Edaravone (A) and natural borneol (B)
in combination on cerebral infarction area

| Group | Model | Nimodipine | A:B = 2:1 | A:B = 1:1 | A:B = 1:2 |
|---|---|---|---|---|---|
| mean ± SD | 27.4 ± 13.4 | 8.8 ± 4.0 * | 9.4 ± 4.9 * | 10.8 ± 5.0 * | 17.2 ± 14.7 |

X ± SD, n = 8;
* P < 0.05, compared with model group.

2.3 Effects on Brain Lesion

Brain lesion in various groups were shown in Table 5. Compared with model group, treatment by Edaravone and natural borneol in ratios of 2:1 and 1:1, and by Nimodipine significantly reduced the severity of brain lesion ($F_{4,35}=5.36$, P=0.002). Compared with model group, treatment by Edaravone and natural borneol in a ratio of 1:2 has the tendency to reduce the severity of brain lesion ($F_{4,35}=5.36$, P=0.239).

TABLE 5

Effects of Edaravone (A) and natural borneol (B) in combination on brain lesion

| Group | Model | Nimodipine | A:B = 2:1 | A:B = 1:1 | A:B = 1:2 |
|---|---|---|---|---|---|
| mean ± SD | 33.2 ± 14.8 | 11.6 ± 5.0 * | 11.7 ± 6.4 * | 11.1 ± 6.8 * | 19.3 ± 18.2 |

X ± SD, n = 8;
* P < 0.05, compared with model group.

Example 18

1. Materials and Methods 1.1 Animals: Healthy male Wistar rats weighing 280-320 g.

1.2 Drugs and Reagents: Edaravone for injection (2 mg/mL) of Example 1, and Edaravone+natural borneol for injection of Examples 5, 7 and 11.

1.3 Methods

Experimental methods and evaluation methods are the same as Example 13.

2. Results 2.1 Effects on Neurological Deficit Symptoms

The score of neurological deficit symptoms were shown in Table 6. Compared with model group, treatment by Edaravone and natural borneol in various ratios, and by Nimodipine significantly ameliorated neurological deficit symptoms ($F_{4,35}=10.31$, P=0.000). It was shown that Edaravone and natural borneol in combination can ameliorate neurological deficit symptoms significantly.

TABLE 6

Effects on neurological deficit symptoms by Edaravone
(A) and natural borneol (B) in combination

| Group | Model | Edaravone (3 mg/kg) | A:B = 2:1 | A:B = 4:1 | A:B = 9:1 |
|---|---|---|---|---|---|
| Mean ± SD | 2.7 ± 0.5 | 0.94 ± 0.46 * | 1.1 ± 0.54 * | 1.3 ± 0.87 * | 1.6 ± 0.55 * |

X ± SD, n = 8;
* P < 0.05, compared with model group.

2.2 Effects on Cerebral Infarction Area

Cerebral infarction areas in various groups were shown in Table 7. Compared with model group, treatment by Edaravone and natural borneol in a ratio of 2:1, and by Edaravone 3 mg/kg significantly reduced cerebral infarction area ($F_{4,35}$=4.62, P=0.03). Compared with model group, treatment by Edaravone and natural borneol in ratios of 4:1 and 9:1 had the tendency to reduce cerebral infarction area ($F_{4,35}$=4.62, P=0.081).

TABLE 7

Effects of Edaravone (A) and natural borneol (B) in combination on cerebral infarction area

| Group | Model | Edaravone (3 mg/kg) | A:B = 2:1 | A:B = 4:1 | A:B = 9:1 |
|---|---|---|---|---|---|
| Mean ± SD | 25.4 ± 14.8 | 9.7 ± 4.6 * | 10.3 ± 5.3 * | 14.6 ± 10.9 | 16.5 ± 11.0 |

X ± SD, n = 8;
* P < 0.05, compared with model group.

2.3 Effects on Brain Lesion

Brain lesions in various groups were shown in Table 8. Compared with model group, treatment by Edaravone and natural borneol in a ratio of 2:1, and by Edaravone 3 mg/kg significantly reduced the severity of brain lesion ($F_{4,35}$=5.78, P=0.04). Compared with model group, treatment by Edaravone and natural borneol in ratios of 4:1 and 9:1 had the tendency to reduce the severity of brain lesion ($F_{4,35}$=5.78, P=0.159).

TABLE 8

Effects of Edaravone (A) and natural borneol (B) in combination on brain lesion

| Group | Model | Edaravone (3 mg/kg) | A:B = 2:1 | A:B = 4:1 | A:B = 9:1 |
|---|---|---|---|---|---|
| Mean ± SD | 32.2 ± 15.1 | 11.6 ± 9.7 * | 13.1 ± 8.3 * | 22.3 ± 17.7 | 23.9 ± 19.8 |

X ± SD, n = 8;
* P < 0.05, compared with model group.

Example 19

1. Materials and Methods 1.1 Animals: 36 New Zealand rabbits, general grade, with body weight of 2.0-3.0 kg, 18 ♂ and 18 ♀ (female and male) respectively.

1.2 Drugs and Reagents: drugs obtained from Examples 12, 13, 14 and 15; 1,2-propylene glycol, 0.9% sodium chloride injection.

1.3 Dosage and Grouping
Solvent 0.9% sodium chloride injection (by weight) 10 mL/kg
vehicle 40% propylene glycol solution (by volume) 10 mL/kg
Edaravone 80 mg/kg (propylene glycol content: 40%)
Edaravone 20 mg/kg (propylene glycol content: 10%)
Combined Edaravone 120 mg/kg (propylene glycol content: 50%)
Combined Edaravone 30 mg/kg (propylene glycol content: 10%)

Combined Edaravone in this Example refers to Edaravone+natural borneol (weight ratio=2:1).

In the above dosage groups, the dosage per day per rabbit was calculated according to actual weight of each rabbit. The test drugs were administered in equal volume according to body weight of respective rabbits.

2. Methods 36 rabbits were numbered and randomly divided into six groups according to the body weight, including 4 dosage groups, "Edaravone+natural borneol (weight ratio=2:1)" 120 mg/kg, 30 mg/kg; "Edaravone" 80 mg/kg, 20 mg/kg; as well as vehicle group (40% propylene glycol solution) and solvent group (0.9% sodium chloride injection). There were 6 rabbits in each group, including 3 males and 3 females each. Rabbits were habituated and observed for 3 days before the test. During the test, rabbits were dosed once at the same time in each morning via marginal ear vein injection. Rabbits in high dosage groups were continuously dosed for 13 days, while in low dosage groups, solvent group and vehicle group for 20 days. The dosage were regulated in accordance with body weight variation. Animal responses, stimulations at injection sites and histopathological examination in kidneys and injection site were used to comprehensively evaluate the toxicity of either combined Edaravone or Edaravone on the rabbits.

3. Results

Hematuria: During the continuous intravenous administration, temporary hematuria occurred 30 min to 2 hr after the administration in groups treated with Edaravone 80 mg/kg or 20 mg/kg, combined Edaravone 120 mg/kg or 30 mg/kg, or 40% propylene glycol solution 10 mL/kg. The incidence of hematuria was 100% in Edaravone 80 mg/kg group, 100% in Edaravone 20 mg/kg group, 100% in combined Edaravone 120 mg/kg group, 50% in combined Edaravone 30 mg/kg group, 100% in 40% propylene glycol solution 10 mL/kg group. However, no hematuria occurred in 0.9% sodium chloride injection group.

gross necropsy and histopathological examinations: 1) gross necropsy: In Edaravone 80 mg/kg group, 3 of 6 rabbits had khaki and swollen kidney having uneven surface, one of the rabbits suffered hepatonecrosis and had a khaki and hard liver. In Edaravone 20 mg/kg group, 3 of 6 rabbits had a swollen kidney. In combined Edaravone 120 mg/kg group, 2 of 6 rabbits had a light-colored and swollen kidney. No obvious changes of kidney were observed in combined Edaravone 30 mg/kg group and 40% propylene glycol solution 10 mL/kg group. 2) Histopathological examination: In Edaravone 80 mg/kg and 20 mg/kg groups and combined Edaravone 120 mg/kg and 30 mg/kg groups, stimulatory changes such as vascular occlusion to varied extents were observed at injection sites. In the above groups, rabbit's kidney lesions were also observed, main manifestations of which were progressive renal lesion such as renal tubular lesion, inflammatory infiltration of mesenchyme, and glomerular lesion. In 40% propylene glycol solution 10 mL/kg group, stimulatory changes such as vascular occlusion also occurred at injection sites, while only mild renal tubular swelling and vacuolar degeneration were observed from their kidneys.

It was concluded from the above experimental results that, in the above dosage conditions, 1: Edaravone and combined Edaravone show substantially similar stimulatory effects on the injection sites of rabbits. 2: Edaravone induces more incidence of hematuria in rabbits than combined Edaravone. 3: Edaravone has higher toxicity on rabbit's kidney than combined Edaravone.

Only some preferred embodiments of the present invention are described as above. It should be noted that the skilled in the art can make further improvements and/or modifications without departing from the spirits of the present invention, which are still claimed in the present invention.

What to be claimed are:

1. A pharmaceutical composition comprising 3-methyl-1-phenyl-2-pyrazolin-5-one and borneol, wherein the composition has synergistic effect in the treatment of cerebrovascular diseases and has reduced toxicity, and wherein the weight ratio of 3-methyl-1-phenyl-2-pyrazolin-5-one to borneol is from 4:1 to 1:1.

2. The pharmaceutical composition according to claim 1, wherein the weight ratio of 3-methyl-1-phenyl-2-pyrazolin-5-one to borneol is from 2:1 to 1:1.

3. The pharmaceutical composition according to claim 1, wherein the borneol is natural borneol.

4. The pharmaceutical composition according to claim 1, wherein the composition further comprises a solvent.

5. The pharmaceutical composition according to claim 4, wherein the solvent is water-soluble organic solvent, or a mixture of water-soluble organic solvent and water.

6. The pharmaceutical composition according to claim 5, wherein the water-soluble organic solvent is propylene glycol.

7. A method of treating a cerebrovascular disease in a subject, comprising administering to the subject effective amount of the pharmaceutical composition according to claim 1.

8. The method according to claim 7, wherein the cerebrovascular disease is ischemic cerebrovascular disease.

9. The method according to claim 7, wherein the cerebrovascular disease is cerebral infarction.

10. The method according to claim 7, wherein the weight ratio of 3-methyl-1-phenyl-2-pyrazolin-5-one to borneol is from 2:1 to 1:1.

11. The method according to claim 7, wherein the borneol is natural borneol.

12. The method according to claim 7, wherein the composition further comprises a solvent.

13. The method according to claim 12, wherein the solvent is water-soluble organic solvent, or a mixture of water-soluble organic solvent and water.

14. The method according to claim 13, wherein the water-soluble organic solvent is propylene glycol.

* * * * *